United States Patent [19]

Tuch

[11] Patent Number: 5,865,814
[45] Date of Patent: *Feb. 2, 1999

[54] BLOOD CONTACTING MEDICAL DEVICE AND METHOD

[75] Inventor: Ronald J. Tuch, Plymouth, Minn.

[73] Assignee: Medtronic, Inc., Minneapolis, Minn.

[ * ] Notice: The term of this patent shall not extend beyond the expiration date of Pat. No. 5,624,411.

[21] Appl. No.: 906,927

[22] Filed: Aug. 6, 1997

Related U.S. Application Data

[62] Division of Ser. No. 473,844, Jun. 7, 1995.

[51] Int. Cl.$^6$ .......................... A61M 25/00; A61M 29/00
[52] U.S. Cl. .......................... 604/265; 424/426; 606/194; 623/1; 623/900
[58] Field of Search .................................. 623/1, 900, 12; 604/266, 265, 890.1, 97, 891.1; 424/424, 426; 606/194

[56] References Cited

U.S. PATENT DOCUMENTS

| | | | |
|---|---|---|---|
| 3,673,612 | 7/1972 | Merril et al. | 3/1 |
| 4,118,485 | 10/1978 | Eriksson et al. | 424/183 |
| 4,268,463 | 5/1981 | Aoyagi et al. | 264/424 |
| 4,321,711 | 3/1982 | Mano | 3/1.4 |
| 4,600,652 | 7/1986 | Solomon et al. | |
| 4,613,665 | 9/1986 | Larm | 536/20 |
| 4,642,242 | 2/1987 | Solomon et al. | 427/2.3 |
| 4,713,073 | 12/1987 | Reinmüller | 623/8 |
| 4,720,512 | 1/1988 | Hu et al. | 523/112 |
| 4,733,665 | 3/1988 | Palmaz | 128/343 |
| 4,786,556 | 11/1988 | Hu et al. | 428/412 |
| 4,800,882 | 1/1989 | Gianturco | 128/343 |
| 4,886,062 | 12/1989 | Wiktor | 128/343 |
| 5,032,666 | 7/1991 | Hu et al. | 528/70 |
| 5,077,372 | 12/1991 | Hu et al. | 528/70 |
| 5,100,668 | 3/1992 | Edelman et al. | 424/422 |
| 5,380,299 | 1/1995 | Fearnot | 604/265 |
| 5,464,650 | 11/1995 | Berg et al. | 427/2.3 |
| 5,569,463 | 10/1996 | Helmus et al. | 427/2.12 |
| 5,605,696 | 2/1997 | Eury et al. | 424/423 |
| 5,609,629 | 3/1997 | Fearnot et al. | 623/1 |
| 5,624,411 | 4/1997 | Tuch | 604/265 |

*Primary Examiner*—Diana Dudash
*Attorney, Agent, or Firm*—Daniel W. Latham; Harold R. Patton

[57] ABSTRACT

A a blood-contacting medical device with improved biocompatibility. The device is coated with a layer of water-soluble heparin, overlaid by a porous polymeric coating through which the heparin can elute. The inclusion of a porous polymer in intimate contact with a heparin on the device controls the administration of heparin following implantation or other blood contact. The adhesion of the coating and the rate at which the heparin is delivered can be controlled by the selection of an appropriate bioabsorbable or biostable polymer.

26 Claims, 2 Drawing Sheets

BLOOD CONTACTING MEDICAL DEVICE AND METHOD

This is a divisional of application Ser. No. 08/473,844 filed on Jun. 7, 1995, pending.

BACKGROUND OF THE INVENTION

This invention relates to intravascular devices for contact with blood having blood-contacting surfaces of improved biocompatibility and particularly to stents for treatment of injuries to blood vessels.

Medical devices which serve as substitute blood vessels, synthetic and intraocular lenses, electrodes, catheters, stents and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body.

As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism. One approach to improved biocompatibility for biomaterials is to attach various "biomolecules" such as growth factors, antimicrobial agents, antithrombogenic agents, and cell attachment proteins to the surface of the material.

Immobilization of polysaccharides such as heparin to biomaterials has been researched extensively to improve bio- and hemocompatibility. The mechanism responsible for reduced thrombogenicity of heparinized materials is believed to reside in the ability of heparin to speed up the inactivation of serine proteases (blood coagulation enzymes) by AT-III. In the process, AT-III forms a complex with a well defined pentasaccharide sequence in heparin, undergoing a conformational change and thus enhancing the ability of AT-III to form a covalent bond with the active sites of serine proteases such as thrombin. The formed TAT-complex then releases from the polysaccharide, leaving the heparin molecule behind for a second round of inactivation.

Usually, covalent immobilization of heparin to a biomaterial consists of activating the material in such a way that coupling between the biomaterial and functional groups on the heparin (—COOH, —OH, —NH$_2$) can be achieved. Thromboresistant surfaces are not necessarily obtained using these processes. Heparin can be bound too tightly to the surface due to the high abundance of functional groups on the heparin, or coupling may result from bonds between the active pentasaccharide sequence on the heparin and the biomaterial, preventing activation of AT-III and thus catalytic deactivation of the proteases. In order to obtain truly anti-thrombogenic surfaces, proper immobilization of the biomolecules is key. Larm presented (in U.S. Pat. No. 4,613,665) a method to activate heparin via a controlled nitrous acid degradation step, resulting in degraded heparin molecules of which a part contains a free terminal aldehyde group. Heparin in this form can be covalently bound to an aminated surface in a reductive amination process. Although the molecule is degraded and as a result shows less catalytic activity in solution, the end point attachment of this type of heparin to a surface results in true anti-thromogenicity due to the proper presentation of the biomolecule to the surface. In this fashion, the molecule is freely interacting with AT-III and the coagulation enzymes, preventing the generation of thrombi and microemboli.

Besides the coupling of heparin via its natural functional groups or through a terminal aldehyde group, coupling of heparin via aldehyde groups randomly introduced into the chain by means of periodate oxidation has also been described. Solomon et al (in U.S. Pat. Nos. 4,600,652 and 4,642,242) and Hu et al (in U.S. Pat. Nos. 4,720,512; 4,786,556; 5,032,666 and 5,077,372) coupled heparin after periodate oxidation to an aminated polyurethane obtaining a material with high loading of stably bound heparin with the inventors claiming excellent antithrombogenicity for the material.

On metal or glass surfaces, the binding of the base layer of such multi-layer coatings can be a problem since there is no organic structure to provide covalent bonds between the metal or glass substrate and the grafted base layer. Others have addressed the problem of binding to metals and glass by applying aminosilanes to adhere to the surface and then attaching the biomolecule to the aminosilane through the amine functionality of the aminosilane. This can be seen in U.S. Pat. No. 5,355,433 issued to Rowland et al in which an aminosilane is used to adhere a heparin molecule to the oxidized tantalum surface of a stent. Aminosilanes are also disclosed for attachment of a heparin molecule to glass or metal surfaces in U.S. Pat. No. 4,118,485 issued to Eriksson et al. However, the use of aminosilanes in coatings of this sort has not been very good in producing a surface with a high level of both bioeffectiveness and stability.

It is therefore an object of the present invention to provide a medical device having a therapeutically significant amount of heparin applied to a blood-contacting surface.

It is also an object of the present invention to provide a stent which may be delivered and expanded in a selected blood vessel without losing a therapeutically significant amount of the heparin applied thereto.

It is also an object of the present invention to provide a heparinized medical device which allows for a sustained release of the heparin.

It is also an object of the present invention to provide a simple method for applying a coating of heparin to a medical device.

SUMMARY OF THE INVENTION

These and other objects are accomplished by the present invention. We have discovered a blood-contacting medical device such as an intravascular stent which includes a coating of heparin, in which the coating includes a porous polymeric overlayer to control the rate of elution of heparin from the surface. The inclusion of a porous polymer in intimate contact with heparin on the device allows the device to flex without losing the heparin. For example, in a stent, the invention allows the heparin to be retained on the stent in a resilient matrix during expansion of the stent and also slows the administration of drug following implantation. While not wishing to be bound by theory, it is believed that the porosity of the overlayer provides improved resistance to cracking as the stent is radially expanded or contracted which makes timed delivery of heparin more certain. The coating can be applied whether the surface has a metallic, glass or polymeric surface. The coating can also be provided by methods which assure carefully controlled dosage.

In one aspect of the invention, the coating may be provided by heparin applied to the surface simply from aqueous solution or dispersion. For example, heparin can be applied from aqueous solution onto a stent body and allowed to dry. The porous polymeric overlayer can then be applied to the heparin coated stent body such that it controls the release of heparin from the coating. The total amount of heparin to be included on the stent can be readily controlled by applying multiple thin coats of the solution while allowing it to dry between coats. For example, a target dosage of drug is determined and the stent body is weighed. A solution of heparin and water is applied to the stent body in successive thin coats with drying and weighing of the stent between coats. When the total weight of coating on the stent indicates that the target dosage has been achieved, no additional heparin solution is applied. The overall coating should be thin enough so that it will not significantly increase the profile of the stent for intravascular delivery by catheter. It is therefore preferably less than about 0.002 inch thick and most preferably less than 0.001 inch thick. The adhesion of the coating and the rate at which the heparin is delivered can be controlled by the selection of an appropriate bioabsorbable or biostable polymer for the porous overlayer. This can be accomplished while maintaining the correct therapeutic dosage by applying to a device which already has a coating containing a desired amount of heparin, a thin coating overlayer or several thin overlayers of a polymer and solvent while drying the device between each coating layer.

In yet another aspect of the invention, the surface concentration of heparin on the device can be adjusted by varying the hydrophilicity/hydrophobicity of the base to which the aqueous drug coating is applied. For example, in a tantalum stent, a coating of a hydrophobic polymer can be applied to the stent as an underlayer to receive the aqueous heparin solution. When applied to this surface, the aqueous solution of heparin forms beads of heparin on some portions of the stent surface while other portions of the surface are relatively free of the drug. The porous overlayer can then be applied over the polymeric underlayer and beads of drug to encapsulate the beads of drug and secure them to the stent surface. If a more uniform surface is desired, a hydrophilic polymer can be applied as an underlayer or the polymeric underlayer can be provided with a plasma treatment to introduce hydrophilic chemical groups onto the polymer surface.

In operation, a stent made according to the present invention can deliver drugs to a body lumen by introducing the stent transluminally into a selected portion of the body lumen and radially expanding the stent into contact with the body lumen. The transluminal delivery can be accomplished by a catheter designed for the delivery of stents and the radial expansion can be accomplished by balloon expansion of the stent, by self-expansion of the stent, or a combination of self-expansion and balloon expansion.

DETAILED DESCRIPTION OF THE INVENTION

Figure 1A:
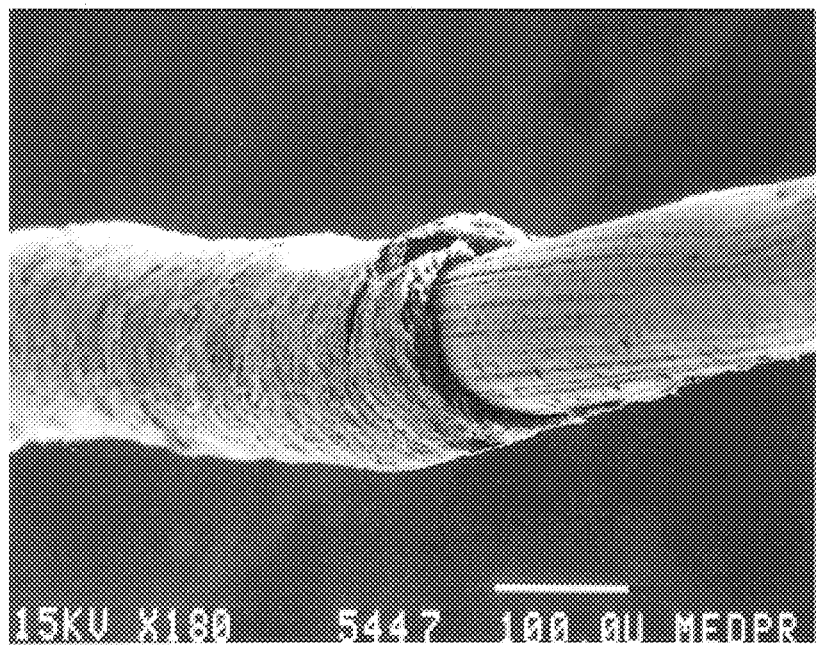
FIGS. 1a, 1b, 1c are SEM micrographs of a porous poly(L-lactic acid) overlayer applied to a stent.

The present invention relates to a method for making a blood-contacting medical device such as an intravascular stent. The blood-contacting portion of the device used in the present invention may be virtually any shape or form, such as plates, strips, films, sheets, fibers, fabrics, filaments, tubing, and cast, extruded or compressed articles, and the like. Examples of devices which may be provided with improved biocompatible surfaces in accordance with this invention include both implantable and extracorporeal devices such as vascular graft tubing, blood oxygenators, intravascular balloons, blood bags, catheters, implantable pulse generators, electrodes, electrical leads, stents, sutures, soft or hard tissue prosthesis, artificial organs and the like. The following description refers to the stent embodiment, but it will be appreciated by those skilled in the art that the invention described may also be applied to many other blood-contacting medical devices.

The underlying structure of the stent can be virtually any stent design, whether of the self-expanding type or of the balloon-expandable type and whether metal or polymeric. Thus metal stent designs such as those disclosed in U.S. Pat. No. 4,733,665 issued to Palmaz, U.S. Pat. No. 4,800,882 issued to Gianturco or U.S. Pat. No. 4,886,062 issued to Wiktor could be used in the present invention. The stent could be made of virtually any bio-compatible material having physical properties suitable for the design. For example, tantalum and stainless steel have been proven suitable for many such designs and could be used in the present invention. Also, stents made with biostable or bioabsorbable polymers such as poly(ethylene terephthalate), polyacetal, poly(lactic acid), poly(ethylene oxide)/poly (butylene terephthalate) copolymer could be used in the present invention. Although the stent surface should be clean and free from contaminants that may be introduced during manufacturing, the stent surface requires no particular surface treatment in order to retain the coating applied in the present invention. Both the inner and outer surfaces of the stent may be provided with the coating according to the present invention.

An aqueous heparin solution is applied to the stent and the water is allowed to evaporate, thereby leaving on the stent surface a coating of heparin. Typically, the solution can be applied to the stent by either spraying the solution onto the stent or immersing the stent in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the stent. In either a coating applied by spraying or by immersion, multiple application steps are generally desirable to provide improved coating uniformity and improved control over the amount of therapeutic substance to be applied to the stent.

In order to provide additional control over the elution of the heparin, a porous polymeric overlayer is also applied to the stent. The polymer chosen must be a polymer that is biocompatible and minimizes irritation to the vessel wall when the stent is implanted. The polymer may be either a biostable or a bioabsorbable polymer depending on the desired rate of release or the desired degree of polymer stability, but a bioabsorbable polymer is probably more desirable since, unlike a biostable polymer, it will not be present long after implantation to cause any adverse, chronic local response. Bioabsorbable polymers that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

With an aqueous coating of heparin placed on the stent, the polymer overlayer is critical to the control of elution from the implanted stent since the heparin is water soluble and would otherwise elute immediately without providing a desired long term benefit. For example, an aqueous coating of heparin can be provided by spraying a solution or dispersion of heparin onto the stent body. When the applied heparin layer is dry, a solution of chloroform and poly(L-lactic acid) can be used to form the overlayer by spraying the polymer solution onto the stent as disclosed above.

The overlayer is preferably provided in porous form. Contrary to expectations, it has been found that the porous overlayer can reduce rather than increase the rate of drug elution. While not wishing to be bound by theory, it is believed that the porous overlayer is less susceptible to cracking as the stent undergoes deformation during handling and implantation. For example, with a Wiktor type stent, the coating is applied to a stent which is in an expanded form. Once the coating is dried, the stent is crimped onto a delivery balloon which causes various stent elements and the coating to bend. During implantation, the delivery balloon expands, again deforming the stent elements and coating. In a very uniform overlayer made with materials which have a limited elasticity, the overlayer can sustain significant cracking during such deformation. These cracks can then act as channels for more rapid elution of heparin from the heparin-rich base coating.

A suitable porous coating can be provided, for example, by phase inversion precipitation of the polymer in the overlayer. According to this technique, a solution of a polymer is prepared in a mixture of two miscible solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous structure. For example, when using poly(L-lactic acid) as the polymer, a suitable solvent composition can include about a 40/60% (w/w) isooctane/chloroform solution. This solution should be mixed carefully to avoid precipitation during the mixing process. The better solvent for the polymer should dissolve the polymer first (i.e. a solution of poly(L-lactic acid) and chloroform should be made first). A mixture of the solvents should then be added to the polymer solution to bring the ingredients to the desired concentration (i.e. a mixture of isooctane and chloroform is added to the poly(L-lactic acid) solution). This mixture is then applied to the stent in the same manner as set forth above. It will be appreciated by those skilled in the art that the nature of the ingredients and the relative concentrations of the ingredients will determine the size of pores. Pores in the range of about 0.5 to 10 microns in diameter may be suitable. Phase inversion precipitation techniques are well known in the manufacture of porous polymeric membranes. (See e.g. van de Witte et al, *Polylactide Membranes: Correlation between phase transitions and morphology*, doctoral thesis, CIP-GEGEVENS KONINKLUKE BIBLIOTHEEK, DEN, HAAG, 1994.) A porous coating may also result under less controlled conditions from application of the overlayer during high humidity conditions in which atmospheric moisture condenses on the stent due to localized cooling of the stent as the solvent evaporates.

The following examples are exemplary of various aspects of the invention.

EXAMPLE 1

Stents were provided with an overlayer of porous poly (L-lactic acid) by a phase inversion precipitation technique. A 40/60% (w/w) isooctane/chloroform solution was used containing 0.5% poly(L-lactic acid). The solution was made by adding 2.0 g of a solution of 5.0% Poly(L-lactic acid) in chloroform to a pre-mixed solution of 8.0 g isooctane and 10.0 g chloroform. An airbrush apparatus (Badger #250-2) was used to apply the solution to Wiktor stents under the following conditions:

Air pressure=30 psi

Burst duration=0.5 second

Nozzle to stent distance=30 mm

Time between bursts=5–7 seconds (coating turns white)

Figure 1B:
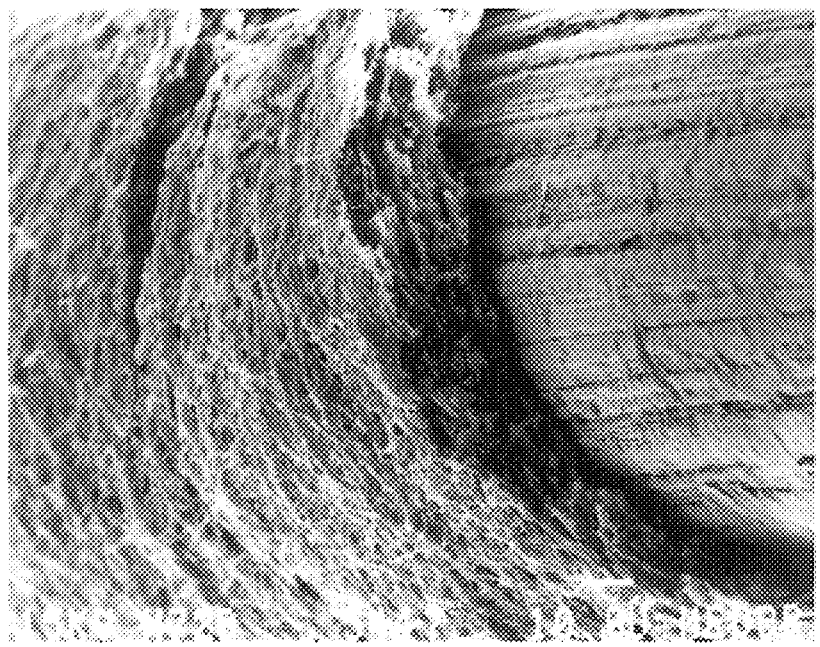
Figure 1C:
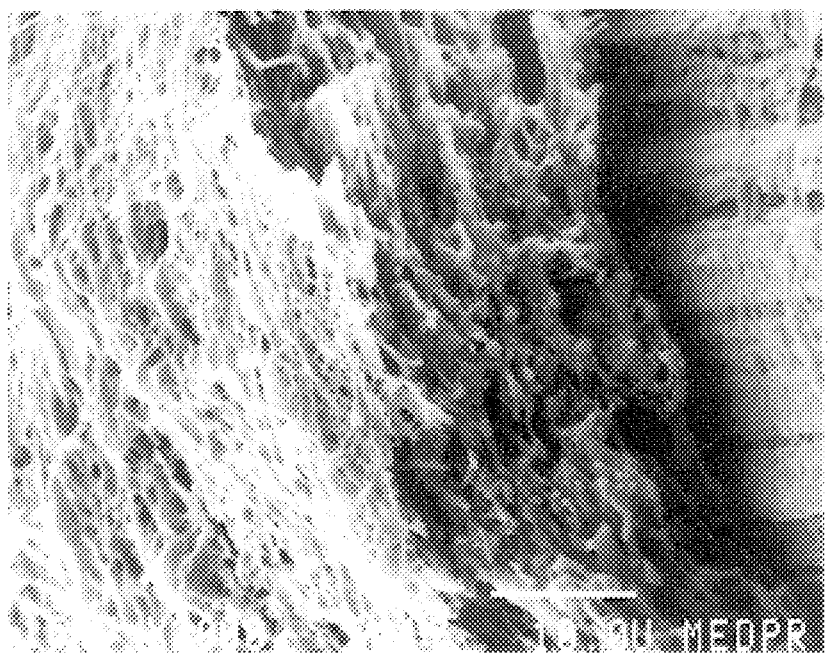

Ambient temperature and humidity Stents were rotated 5/16 of a turn after each burst and sprayed initially with 50 bursts/end. After at least 4 hours of air drying, the stents were fixtured at the other end and the second half was coated. After overnight vacuum drying at 80° C., the stents were weighed. Additional coatings were applied using the same conditions to bring each stent up to the target weight. The completed stents were vacuum dried at 80° C. for 7 days. The stents were tested for mechanical adhesion of the coating during crimping and expansion operations. The coating was finally fractured by straightening out the sinusoidal wave of the stent and the coating was pulled off with a tweezers to produce the SEM micrographs shown on FIGS. 1a–1c of the coating at 180X, 720X and 2000X respectively.

EXAMPLE 2

Stents were provided with a multi-layer heparin-eluting coating. A 1% solution of poly(L-lactic acid) in chloroform was used to provide an underlayer for the heparin-coated stents. This solution was applied by spraying onto the stents with an airbrush in substantially the same manner as set forth in the examples above such that thin underlayer was provided. A 2% heparin solution was prepared with sterile water. The heparin solution was applied with an airbrush. A poly(L-lactic acid) overlayer was then applied by airbrush from a 1% solution in chloroform. High humidity conditions caused the formation of a cloudy, porous overlayer. The amounts of material on each stent is given in Table 1.

TABLE 1

| Stent | Stent Wt(g) | Underlayer(mg) | Heparin(mg) | Overlayer(mg) |
|---|---|---|---|---|
| 1 | 0.02002 | 0.34 | 0.15 | 0.0 |
| 2 | 0.02006 | 0.35 | 0.17 | 0.26 |
| 3 | 0.02008 | 0.36 | 0.14 | 1.17 |
| 4 | 0.02009 | 0.30 | 0.34 | 0.25 |
| 5 | 0.01993 | 0.35 | 0.40 | 1.11 |
| 6 | 0.01922 | 0.32 | 0.40 | 1.89 |
| 7 | 0.02001 | 0.52 | 0.73 | 0.31 |
| 8 | 0.01906 | 0.37 | 0.75 | 1.17 |
| 9 | 0.01901 | 0.42 | 0.70 | 2.07 |

Each stent was crimped onto an angioplasty balloon and expanded. Elution tests were run on the expanded stents in phosphate buffered saline solution with aliquots withdrawn at various times up to 44 days. Results were as set forth in Table 2.

TABLE 2

| Stent | Units eluted | % Recovery | 80% Elution (days) |
|---|---|---|---|
| 1 | 26 | 94 | 0 |
| 2 | 21 | 65 | 2 |
| 3 | 10 | 40 | 18 |
| 4 | 50 | 78 | 1 |
| 5 | 48 | 64 | 18 |
| 6 | 38 | 51 | 28 |
| 7 | 131 | 96 | 1 |
| 8 | 121 | 86 | 18 |
| 9 | 111 | 85 | 18 |

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A medical device for use in contact with circulating blood comprising:

(a) a medical device having a blood-contacting surface;

(b) a first coating layer on the blood-contacting surface consisting essentially of water soluble heparin; and (c) a second coating layer comprising a porous polymer overlaying the first coating layer such that heparin is elutable from the medical device through the second coating layer.

2. A device according to claim 1 wherein the blood-contacting surface has a metal surface.

3. A device according to claim 1 wherein the blood-contacting surface has a polymeric surface.

4. A device according to claim 1 wherein the polymer is a bioabsorbable polymer.

5. A device according to claim 4 wherein the polymer is selected from the group consisting of poly(lactic acid), poly(lactide-co-glycolide) and poly(hydroxybutyrate-co-valerate).

6. A device according to claim 1 wherein the polymer is a biostable polymer.

7. A device according to claim 6 wherein the polymer is selected from the group consisting of silicones, polyurethanes, polyesters, vinyl homopolymers and copolymers, acrylate homopolymers and copolymers, polyethers and cellulosics.

8. A device according to claim 1 wherein the device is a radially expandable intravascular stent.

9. A device according to claim 1 in which the porous polymer has average pore diameter in the range of about 0.5–10 microns.

10. A medical device for use in contact with circulating blood comprising:

(a) medical device having a blood-contacting surface;

(b) a first coating layer on the blood-contacting surface comprising a hydrophilic polymer;

(c) a second coating layer comprising water soluble heparin overlaying the first coating layer; and (d) a third coating layer comprising a porous polymer overlaying the second coating layer such that heparin is elutable from the medical device through the third coating layer.

11. A device according to claim 10 wherein the blood-contacting surface has a metal surface.

12. A device according to claim 10 wherein the blood-contacting surface has a polymeric surface.

13. A device according to claim 10 wherein the porous polymer is a bioabsorbable polymer.

14. A device according to claim 13 wherein the bioabsorbable polymer is selected from the group consisting of poly(lactic acid), poly(lactide-co-glycolide) and poly(hydroxybutyrate-co-valerate).

15. A device according to claim 10 wherein the porous polymer is a biostable polymer.

16. A device according to claim 15 wherein the biostable polymer is selected from the group consisting of silicones, polyurethanes, polyesters, vinyl homopolymers and copolymers, acrylate homopolymers and copolymers, polyethers and cellulosics.

17. A device according to claim 10 wherein the device is a radially expandable intravascular stent.

18. A medical device for use in contact with circulating blood comprising:

(a) medical device having a blood-contacting surface;

(b) a first coating layer on the blood-contacting surface comprising a hydrophobic polymer;

(c) a second coating layer comprising water soluble heparin overlaying the first coating layer; and (d) a third coating layer comprising a porous polymer overlaying the second coating layer such that heparin is elutable from the medical device through the third coating layer.

19. A device according to claim 18 wherein the second coating layer comprises beads of heparin, and wherein the third coating layer encapsulates the beads of heparin.

20. A device according to claim 18 wherein the blood-contacting surface has a metal surface.

21. A device according to claim 18 wherein the blood-contacting surface has a polymeric surface.

22. A device according to claim 18 wherein the porous polymer is a bioabsorbable polymer.

23. A device according to claim 22 wherein the bioabsorbable polymer is selected from the group consisting of poly(lactic acid), poly(lactide-co-glycolide) and poly(hydroxybutyrate-co-valerate).

24. A device according to claim 18 wherein the porous polymer is a biostable polymer.

25. A device according to claim 24 wherein the biostable polymer is selected from the group consisting of silicones, polyurethanes, polyesters, vinyl homopolymers and copolymers, acrylate homopolymers and copolymers, polyethers and cellulosics.

26. A device according to claim 18 wherein the device is a radially expandable intravascular stent.

* * * * *